United States Patent [19]

Yamada et al.

[11] Patent Number: 5,288,389
[45] Date of Patent: Feb. 22, 1994

[54] OXYGEN SENSOR WITH HIGHER RESISTANCE TO REPEATED THERMAL-SHOCKS AND SHORTER WARM-UP TIME

[75] Inventors: Tessho Yamada; Akio Mizutani, both of Nagoya; Nobuhiro Hayakawa, Chita, all of Japan

[73] Assignee: NGK Spark Plug Co., Ltd., Nagoya, Japan

[21] Appl. No.: 32,187

[22] Filed: Mar. 15, 1993

Related U.S. Application Data

[63] Continuation of Ser. No. 746,010, Aug. 12, 1991, abandoned, which is a continuation-in-part of Ser. No. 330,524, Mar. 10, 1989, abandoned.

[30] Foreign Application Priority Data

Apr. 1, 1988 [JP] Japan .................................. 63-81785
Mar. 22, 1989 [JP] Japan .................................. 1-69832

[51] Int. Cl.$^5$ .................................. G01N 27/419
[52] U.S. Cl. .................................. 204/425; 204/426
[58] Field of Search .................. 204/153.18, 421–429

[56] References Cited

U.S. PATENT DOCUMENTS

| | | |
|---|---|---|
| 4,450,065 | 5/1984 | Yamada et al. .................. 204/425 |
| 4,505,806 | 3/1985 | Yamada .................. 204/425 |
| 4,505,807 | 3/1985 | Yamada .................. 204/425 |
| 4,574,627 | 3/1986 | Sakurai et al. .................. 204/426 |
| 4,722,779 | 2/1988 | Yamada et al. .................. 204/426 |
| 4,765,880 | 8/1988 | Hayakawa et al. .................. 204/426 |

*Primary Examiner*—T. Tung
*Attorney, Agent, or Firm*—Sughrue, Mion, Zinn, Macpeak & Seas

[57] ABSTRACT

An oxygen sensor including, at least, a) an oxygen pump element having a solid electrolyte plate and two porous electrodes, one on each surface of the solid electrolyte plate, b) a gas diffusion chamber facing one of the porous electrodes, and c) a gas diffusion path connecting the gas diffusion chamber and the ambience of the oxygen sensor, is defined its thickness between 0.7 to 1.25 mm, and its width between 2.8 to 4.0 mm. The restricted size renders higher resistance against repeated thermal shocks, and shorter warming-up time, which leads to greater accuracy and higher responsiveness in the oxygen content measurement.

1 Claim, 15 Drawing Sheets

LAMBDA FIXED AT 0.8, &
ELEMENT TEMPERATURE IS FIXED AT 800°C

MEASURING VOLUME 0.23 mm³

LAMBDA FIXED AT 0.8, &
ELEMENT TEMPERATURE IS FIXED AT 800°C

MEASURING VOLUME 0.75 mm³

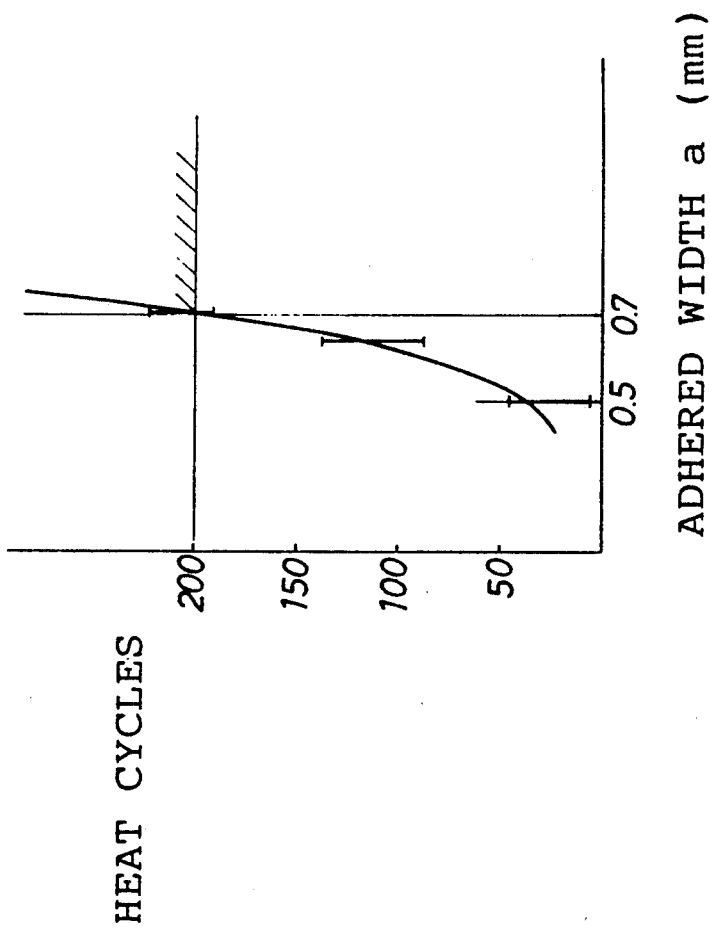

OXYGEN SENSOR WITH HIGHER RESISTANCE TO REPEATED THERMAL-SHOCKS AND SHORTER WARM-UP TIME

This is a continuation of application Ser. No. 07/746,010, filed Aug. 12, 1991, which in turn in a continuation of application Ser. No. 07/330,524 filed on Mar. 10, 1989, both now abandoned.

BACKGROUND

This invention relates to an oxygen sensor for sensing the oxygen ion content of the exhaust gas from an internal combustion engine to control the air/fuel ratio in the combustion chamber. Especially, it relates to the oxygen sensor that uses an oxygen-conductive solid electrolyte material.

Oxygen sensors are used in an automobile engine to control the air/fuel ratio in the combustion chamber around the stoichiometric value, so that the fuel consumption is improved and the exhaust gas is purified. A known oxygen sensor includes an oxygen sensing element having an ion-conductive solid electrolyte plate on which porous electrodes are printed. The sensing element generates a voltage corresponding to the difference in oxygen content between the object gas (exhaust gas) and the reference air.

A recent trend of engine control is to bring the air/fuel ratio not only to the stoichiometric value but to any value according to the operating conditions of the engine to obtain better engine performance as well as to further improve the fuel efficiency and emission. Oxygen sensors appropriate to this need of variable air/fuel ratio control have been developed as, for example, in Japanese Published Unexamined Patent Application Nos. S52-72286 and S53-66292. In these sensors, a gas diffusion chamber is formed facing one of the electrodes of a solid electrolyte plate, and a certain voltage is applied between the electrodes to introduce the object gas into the chamber by diffusion process. The electrical current between the electrodes at that time shows the oxygen content of the object gas.

Another type of oxygen sensor is disclosed in Japanese Published Unexamined Patent Application No. S60-36032 where the oxygen sensor includes an oxygen pump element and an oxygen concentration cell element which are placed parallel to each other forming the gas diffusion chamber between them. Electric current to the oxygen pump element is controlled to keep the voltage between the electrodes of the oxygen concentration cell element constant, where the amount of current shows the oxygen content.

One big problem about the conventional oxygen sensors is that it takes a long time until the sensor becomes active after the engine operation starts. During the period (warm-up period), the engine air/fuel ratio feedback control is impossible. For this reason, recent oxygen sensors are equipped with heaters. But, the heating speed should be limited to a rather lower degree because too rapid heating causes thermal shock on the oxygen sensor which may damage the sensor element.

SUMMARY OF THE INVENTION

One object of the present invention is to make an oxygen sensor that is strong against such thermal shocks. Another object is to provide an oxygen sensor that can be operable soon after start of the engine. Still other object is to make a compact, accurate oxygen sensor suitable for sophisticated precise engine controls.

The oxygen sensor of the present invention has, at least, an oxygen pump element, a gas diffusion chamber and a gas diffusion path. The oxygen pump element is composed of a solid electrolyte plate, and a porous electrode placed on each surface of the solid electrolyte plate. The gas diffusion chamber faces one of the porous electrodes. The gas diffusion path communicates the gas diffusion chamber with the ambience of the oxygen sensor. The feature point of the invention is that the dimensions of the elements are defined as follows: the thickness of the oxygen sensor is 0.7 to 1.25 mm; and its width is 2.8 to 4.0 mm. Since the gas diffusion rate is regulated by the dimensions of the gas diffusion chamber, the thickness of the gas diffusion chamber is preferably between 20 to 100 microns and its volume is preferably between 0.05 to 1.0 $mm^3$ in order to obtain better accuracy in oxygen sensing and quicker response to the change in the oxygen content of the object gas.

The solid electrolyte is made by, for example: yttria-zirconia solid solution; calcia-zirconia solid solution; solid solution of cerium-dioxide, thorium-dioxide or hafnium-dioxide; perovskite solid solution; or solid solution of trivalent-metal-oxides.

The porous electrode is made, for example, by the following process. Platinum powder and rhodium powder are put into a solvent to make paste. The paste is printed on the solid electrolyte plate forming a certain electrode pattern by the thick-film technology, and then the paste is fixed by baking at a high temperature.

The outer electrode of the oxygen pump element that contacts the object gas is preferably covered by a protective layer. The protective layer is made, for example, by the thick-film technology using alumina, spinel zirconia, or mullite. No protective layer is needed on the inner electrode facing the gas diffusion chamber because quicker response to the object gas infiltrating through the solid electrolyte is preferred.

Typically, the gas diffusion chamber is formed between the oxygen pump element and an oxygen concentration cell element. The two elements are attached together with a spacer plate having a hole between them, and the hole forms the gas diffusion chamber. The spacer is made of, for example, alumina, spinel, forsterite, steatite or zirconia.

The gas diffusion path can be filled with porous material to increase the diffusion resistance. The volume of the gas diffusion chamber defined above or in the claim does not include the volume of the gas diffusion path. The gas diffusion chamber volume is almost determined by the area of the electrode of the oxygen pump element and the thickness of the gas diffusion chamber, i.e., the gap length between the oxygen concentration cell element and the oxygen pump element.

Generally, a heater is attached to the oxygen sensor on its outer surface. The heater is separately prepared in order to prevent electrical disturbance to the sensor from the heating wire. The heating wire can be formed on the same surface as and surrounding the porous electrode.

The oxygen sensor of the present invention needs at least the oxygen pump element and the gas diffusion chamber, so it may include oxygen sensors: having the pump element and an oxygen concentration cell element; having no oxygen concentration cell element; having titania (titanite) sensor, instead of the oxygen concentration cell element, placed parallel to the oxygen pump element; having an oxygen concentration cell element and a reference air (atmospheric-air) chamber facing the outer porous electrode opposite to the gas diffusion chamber with respect to the oxygen concentration cell element; and having an internal reference oxygen source connected to the ambient air or to the gas diffusion chamber via a diffusion resistance formed by the porous electrode covered with a shield layer.

The oxygen sensor of the present invention defined by the dimensions has strength greater than a certain level, and the heat capacity is small because the size is rather small. The small size brings about a strong resistance against breakage caused by repeated thermal shocks due to rapid heating and rapid cooling. This enables a rapid warming-up of the oxygen sensor when the engine operation starts.

Since the gas diffusion is regulated by the gas diffusion path, the frequency response of an oxygen sensor is determined by the volume of the gas diffusion chamber (measuring volume). If the thickness (gap) of the gas diffusion chamber is small, the small chamber volume becomes more regulatory to the gas diffusion speed than the gas diffusion path resistance, resulting in deteriorated measurement accuracy. If the gap is too large, on the contrary, the pumping rate of the oxygen pumping element cannot follow a rapid change in the oxygen concentration of the object gas. The defined dimensions of the gas diffusion chamber gives the optimal balance of the measurement accuracy and responsiveness.

BRIEF EXPLANATION OF THE ATTACHED DRAWINGS

FIG. 16 is a graph showing the relationship between the adhesion width and the tolerable number of heat cycles.

DETAILED DESCRIPTION OF PREFERRED EMBODIMENTS

Figure 1:
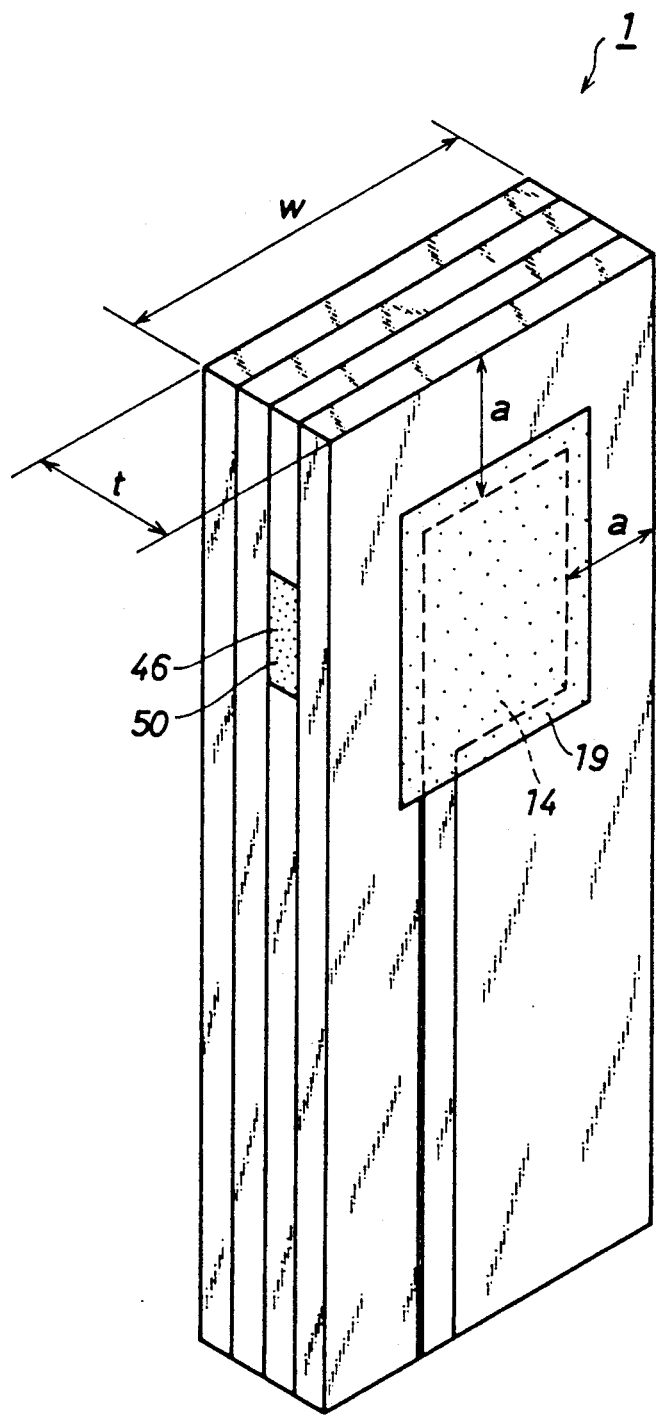
FIG. 1 is a perspective view of an oxygen sensor embodying the present invention.
Figure 2:
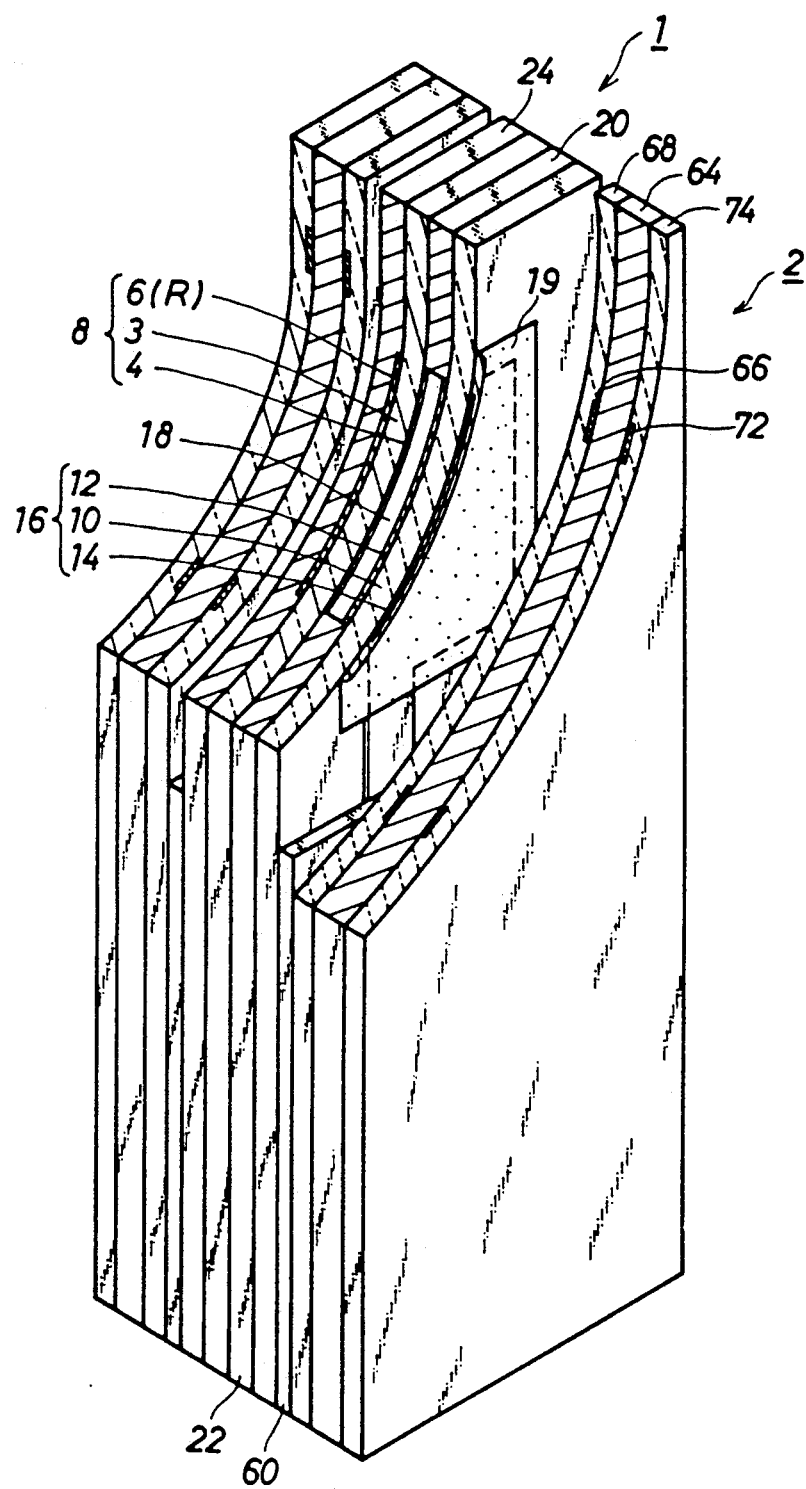
FIG. 2 is a broken view of the oxygen sensor.
Figure 3:
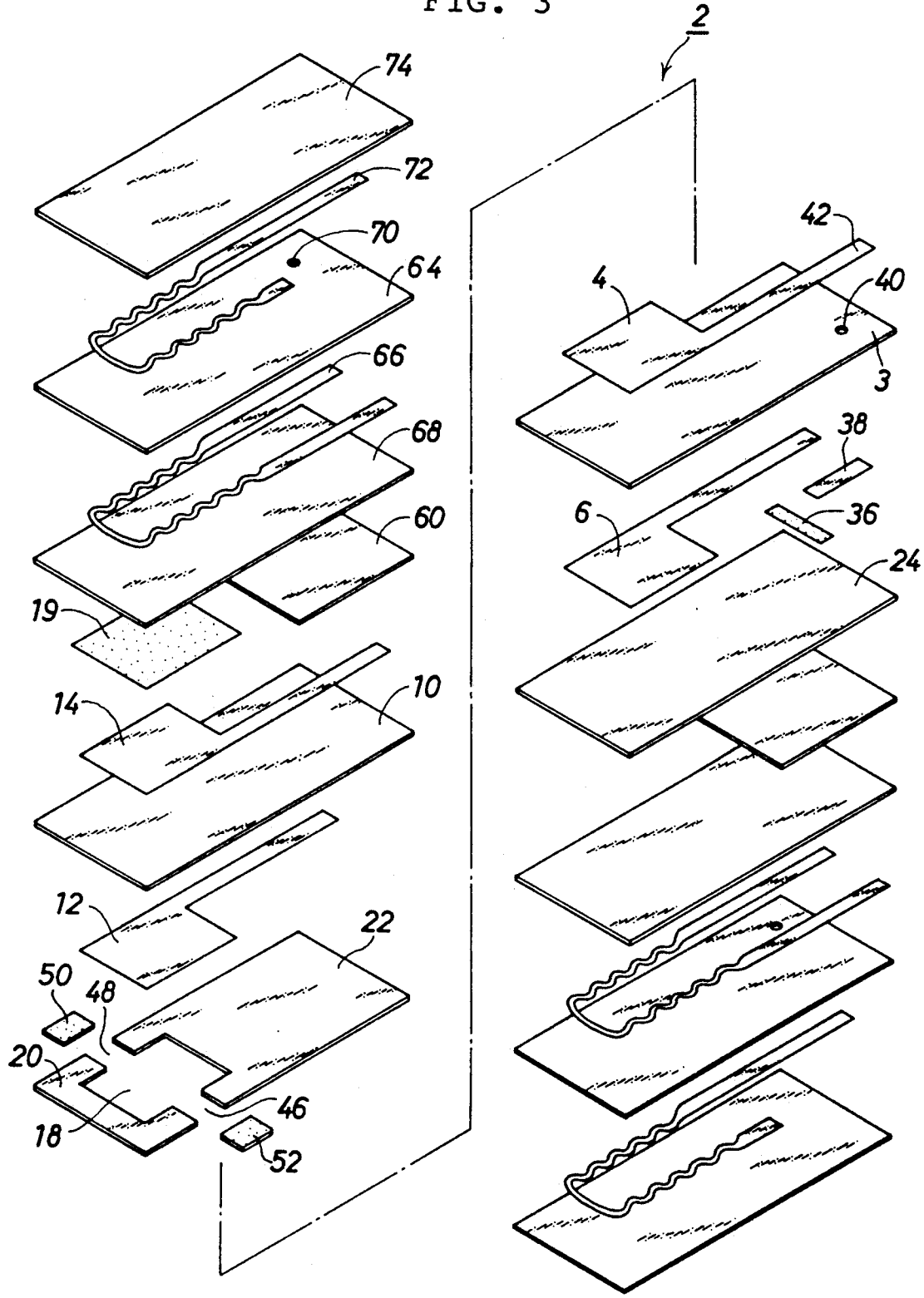
FIG. 3 is a construction diagram of the oxygen sensor.

As shown in FIG. 2, an oxygen sensor 1 embodying the present invention is sandwiched by two heaters 2, which are not shown in FIG. 1 for simplicity, with a small gap between each heater 2 and the sensor 1. The oxygen sensor 1 has an oxygen concentration cell element 8 and an oxygen pump element 16. The oxygen concentration cell element 8 is composed of a solid electrolyte plate 3, and porous electrodes 4 and 6 formed on opposite surfaces of the solid electrolyte plate 3. The oxygen pump element 16 is also composed of a solid electrolyte plate 10, and porous electrodes 12 and 14 on their opposite surfaces. Between the two elements 8 and 16 are inner spacers 20 and 22 to form a gas diffusion chamber 18. The oxygen sensor 1 further includes, as shown in FIG. 3, a shield layer 24 placed on the outer electrode 6 of the oxygen concentration cell element 8, and a protective layer 19 for the porous electrode 14.

The solid electrolyte plate 10 of the oxygen pump element 16, which has dimensions as shown in Table 1, is made mainly of a solid solution of yttria and zirconia. Each of its porous electrodes 12 and 14 has an area of 8 mm$^2$, and is made of platinum mixed with yttria zirconia solid solution.

The oxygen concentration cell element 8 is also formed of, similarly to the oxygen pump element 16, solid electrolyte plate 3 of an yttria-zirconia solid solution, and porous electrodes 4 and 6 similar to the electrodes 12 and 14.

The shield layer 24 is made of zirconia solid solution, and insulates the outer electrode 6 from the ambient object gas in order to use the outer electrode 6 of the oxygen concentration cell element 8 as an internal reference oxygen source R. The outer porous electrode 6 is formed so that, when it is used as the internal reference oxygen source, the oxygen gas generated within the electrode 6 is led to the gas diffusion chamber 18. As shown in FIG. 3, a gas diffusion path having a certain diffusion resistance is formed by a porous insulator 36, a conductive member 38, a through-hole 40 and a lead 42 of the inner porous electrode 4. The porous insulator 36 is made of alumina and the conductive member 38 is made of the same material as the porous electrode 6. The oxygen gas generated in the porous electrode 6 diffuses through the diffusion path.

The internal U-shaped spacers 20 and 22 between the oxygen concentration cell element 8 and the oxygen pump element 16 are made of alumina, and are oppositely placed to form the gas diffusion chamber 18 at the inner electrodes 4 and 12. The spacers 20 and 22 are separated by a small distance to form paths 46 and 48 between them for introducing ambient object gas into the gas diffusion chamber 18. Porous bricks 50 and 52 made of alumina fill the paths 46 and 48 to regulate the gas diffusion.

TABLE 1

| element | Sensor | | |
|---|---|---|---|
| | Thickness (mm) | Width (mm) | Length (mm) |
| Solid Electrolyte Substrate | 0.36 | 3.6 | 45 |
| Porous Electrode | — | 2.0 | 4.0 |

TABLE 1-continued

| element | Sensor Thickness (mm) | Width (mm) | Length (mm) |
| --- | --- | --- | --- |
| Internal Spacer | 0.06 | — | — |
| Insulator | 0.36 | 3.6 | 45 |
| Gas Diffusion Chamber | 0.06 | 2.0 | 4.0 |

Normally, an insulating cover of 10 to 20 micron thick is formed on the outer surface of the oxygen sensor 1 except on the porous electrode 14, but it is not shown in FIGS. 1 and 2 for simplicity.

Figure 4:
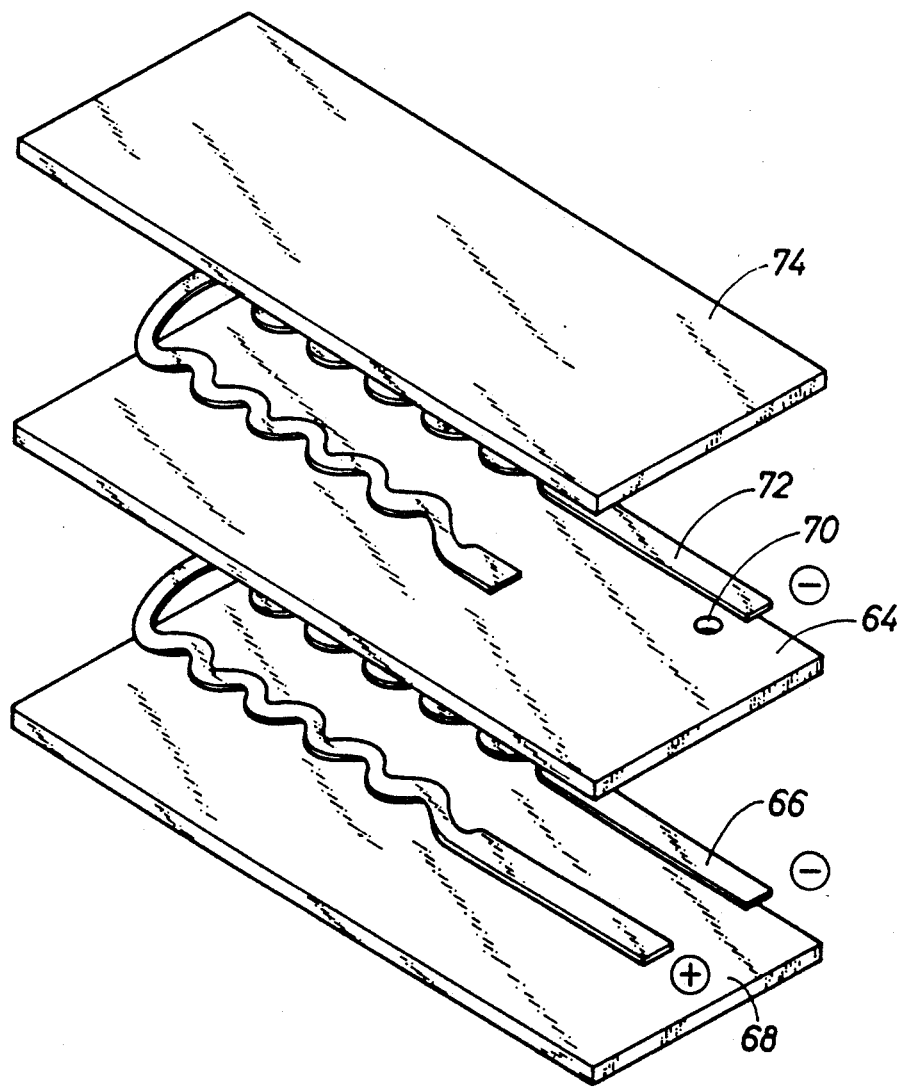
FIG. 4 is a construction diagram of a heater for the oxygen sensor.

The heater 2, having dimensions as in Table 2, is placed on both sides of the oxygen sensor 1 via an external heat-resistant-cement spacer 60 of 100 micron thick, as shown in FIG. 2. As shown in FIG. 4, the heater 2 has a U-shaped wavy heating pattern 66 on the side of s substrate 64 facing the oxygen sensor 1. The heating pattern 66 is covered by an inner alumina laminate film 68. On the other side of the substrate 64 is another pattern 72 which connects to the heating pattern 66 via a through hole 70. The second pattern 72 prevents electrical migration and is covered by an outer laminate film 74.

TABLE 2

| element | Heater Thickness (mm) | Width (mm) | Length (mm) |
| --- | --- | --- | --- |
| External Spacer | 0.1 | 3.6 | 45 |
| Inner Laminate Sheet | 0.3 | 3.6 | 45 |
| Substrate Sheet | 0.5 | 3.6 | 45 |
| Outer Laminate Sheet | 0.3 | 3.6 | 45 |

The second pattern 72 has almost the same shape as the heating pattern 66, and connects only to the cathode of the heating pattern via the through-hole 70. The second pattern 72 prevents the heating pattern 66 from breaking by the migration of even small amount of flux ingredients, such as $SiO_2$, CaO, and MgO, in the substrate 64 between the anode and cathode of the heating pattern 66 by the high temperature and high applied voltage. That is, the function of the second pattern 72 is to enhance migration of such ingredients between the heating pattern 66 and itself to decrease the migration among the heating pattern 66.

Manufacturing

The manufacturing process of the oxygen sensor 1 and the heater 2 is now explained according to FIG. 3.

First, green sheets for the solid electrolyte substrate plate 3 and 10 of the oxygen pump element 16 and the oxygen concentration cell element 8 are formed from a mixture of yttria-zirconia powder, 2.5 wt. % silica (as a baking adhesive), PVB type binder and organic solvent, using the doctor-blade method.

Then the porous electrodes 4, 6, 12 and 14 are printed on the green sheets by the following processes. Platinum powder having specific surface area of less than 10 $m^2/g$ (preferably 4 to 6 $m^2/g$) including appropriate powder material of 16 wt. %, and cellulose or PVB binder are put into solvent such as butyl Carbitol to make paste. The paste is printed on the green sheets through a screen having a pattern hole. Alumina paste is further spread on the outer electrode 14 of the oxygen pump element 16, which will be the protective layer 19.

Green alumina sheets for the internal spacers 20 and 22 are formed, and are put on the oxygen pump element 16. Paste of another alumina material is filled in the gap between the arms of the internal spacers 20 and 22 to form the gas diffusion regulating path 50 and 52.

The oxygen concentration cell element 8, pump element 16 and internal spacers 20 and 22 are stacked together, and the shield layer 24 is pressed onto the stack. The stack is baked at 1500° C. for 1 hour to make the oxygen sensor 1.

The heaters 2 are made separately from the oxygen sensor 1. The heating pattern 66 and the second pattern 72 are printed on the green substrate sheet 64, and the laminate films 68 and 74 are spread on them. The raw material is baked to make a heater 2. The heaters 2 are attached at both sides of the baked oxygen sensor 1 with external spacers 60 between them using heat-resistant inorganic adhesive.

Function

The oxygen sensor 1 works as follows. First, a preset voltage (e.g., 5 V) is applied through a preset resistance (e.g., 250 k-ohm) between the porous electrodes 4 and 6 of the oxygen concentration cell element 8, with the outer electrode 6 used for anode, and the inner electrode 4 for cathode. This causes an electric current through the electrolyte plate 3 and, accordingly, oxygen is transported from the gas diffusion chamber 18 to the internal reference oxygen source R (which is actually the outer electrode 6).

When the oxygen partial pressure in the internal reference oxygen source R becomes greater than that in the gas diffusion chamber 18, a voltage generates between the electrodes 4 and 6 according to the ratio of the partial pressures. The voltage changes stepwise across the stoichiometric value of the air/fuel ratio (i.e., between "rich" and "lean" states of the gas in the gas diffusion chamber 18), and the voltage difference is an order of 100 mV.

The oxygen pump element 16 pumps oxygen from the gas diffusion chamber 18 to the ambience, or vice versa, to keep the gas state in the gas diffusion chamber 18 substantially at the stoichiometric value (lambda=1) regardless of the ambient gas state. That is, the air/fuel ratio of the object gas (exhaust gas of the internal combustion engine) is given by the electrical current Ip of the oxygen pump element 16 when the voltage between the electrodes 4 and 6 of the oxygen concentration cell element 8 is a predetermined value. Alternatively, the air/fuel ratio can be given by the voltage between the electrodes 4 and 6 of the oxygen concentration cell element 8 when the oxygen pump element 16 pumps a constant oxygen flow with a fixed pump current Ip.

Tests

Several tests on the oxygen sensors according to the present invention and comparative conventional oxygen sensors are now described. Tests 1 and 2 are for the effect of sensor dimensions on thermal-shock resistance. Tests 3, 4 and 5 are for the warming-up characteristics of the sensors. Test 6, 7 and 8 are for the effect of the volume of the measuring chamber on the responsiveness of the sensors. Test 9 is for the effect of the adhered width on the tolerable number of heat cycles.

test 1

Figure 5:
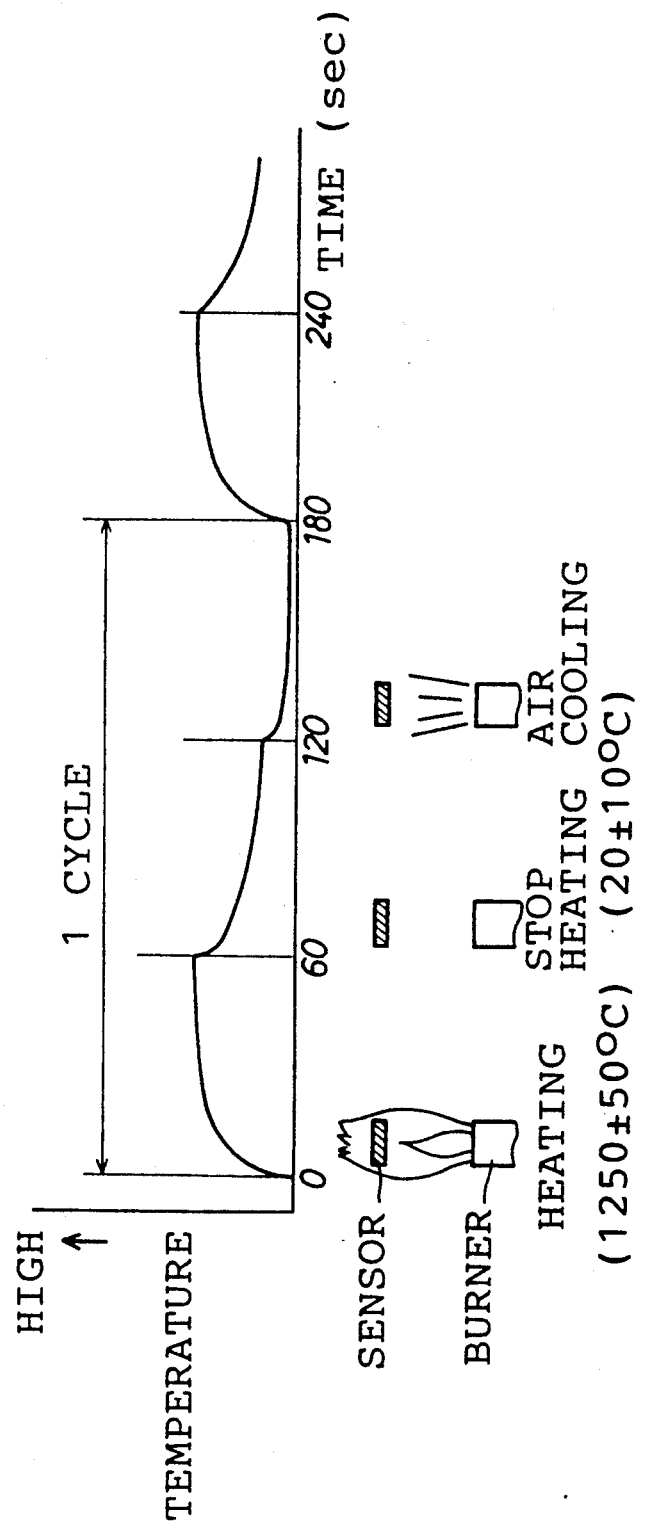
FIG. 5 shows temperature change of the element in the repeated-heating test.

Oxygen sensors having various widths w and thicknesses t (FIG. 1) are prepared, and a repeated-heating test is made for the sensors. One cycle of the test is composed of, as shown in FIG. 5: heating in a burner flame of 1250±50° C. for 60 seconds; natural cooling in 20±10° C. for 60 seconds; and blow cooling with 20±10° C. air for 60 seconds.

First, thermal-shock resistance is tested on sensors having fixed width w of 4.0 mm and various thicknesses t. The thermal shock resistance is measured by the tolerable maximum number of the heating-test cycles until the substrate of the sensor allows gas diffusion through its thickness. The criterion for the gas diffusivity is the cycle number at which the voltage Vs generated by the oxygen concentration cell element (cell voltage) becomes less than 800 mV under the condition that the pump current Ip is 0 in "rich" gas of 800° C.

Figure 6:
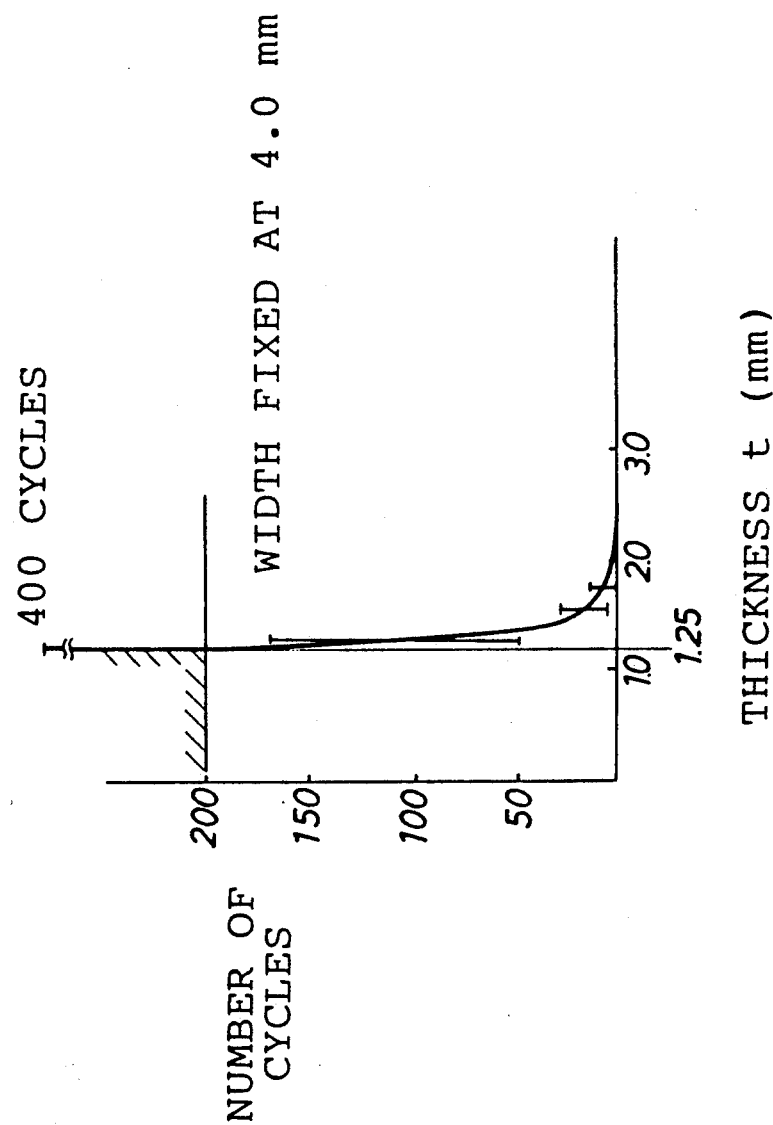
FIG. 6 is a graph showing the relationship between the element thickness and the tolerable number of repeated-heating test cycles.

The test result is shown in FIG. 6, where sensors with thickness t less than 1.25 mm have excellent thermal-shock resistance.

test 2

Figure 7:
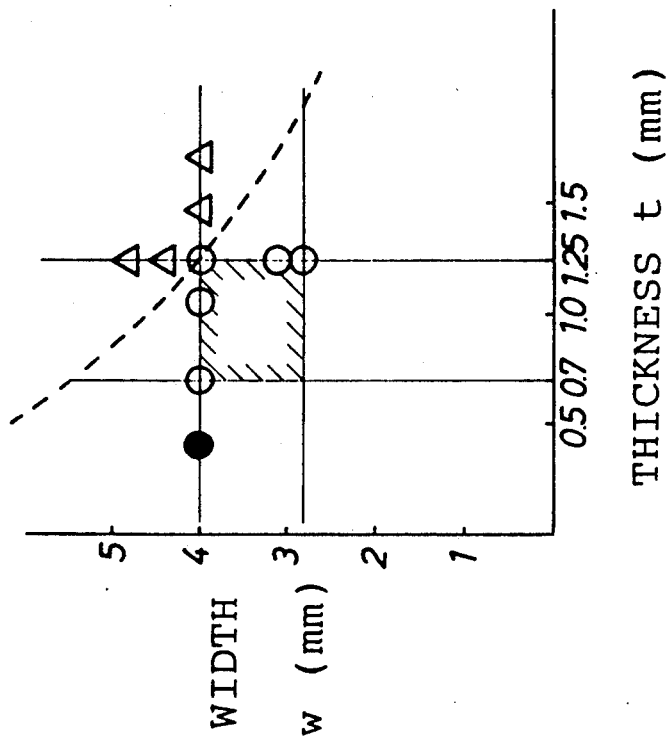
FIG. 7 is a graph showing the relationship between the repeated-heating test results and the thickness/width of the element.

Thermal-shock test results are summarized in FIG. 7 for sensors having various widths w and thicknesses t. In the figure, an open circle shows that the sensor of those dimensions endured more than 200 cycles of the repeated-heat test, a triangle shows that the sensor allows gas leakage after fewer 200 cycles, and the solid circle shows that the gas leakage occurs because the electrolyte plate is too thin.

As seen in FIG. 7, sensors of thickness t between 0.7 to 1.25 mm (preferably 0.9 to 1.15 mm) and width w between 2.8 to 4.0 mm have high thermal-shock resistance (i.e., have high gas leakage resistance even after more than 200 cycles of the repeated-heating test).

Figure 8:
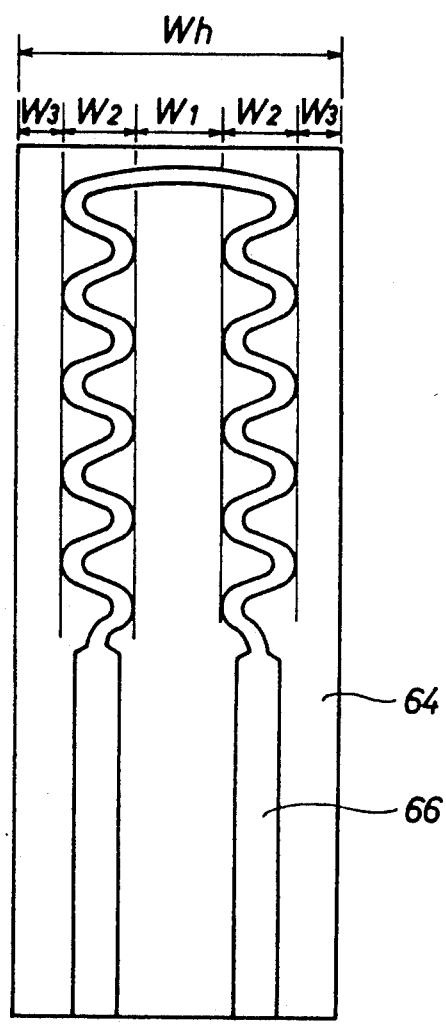
FIG. 8 shows a pattern of the heating wire.

The lower limit 2.8 mm of the width w of the sensors comes from the design restriction as follows. As shown in FIG. 8, the central margin w1 of the heating pattern of the heater is preferably more than 1.5 times the thickness tb of the substrate sheet (specifically, w1 is more than 0.8 mm) in order to sufficiently prevent the migration. The width of the heating wire needs more than 0.4 mm due to printing tolerance and for sufficient resistance, and the overall width w2 of the wavy portion requires more than 0.8 mm. The width w3 of margins for adhering the heater to the sensor needs 0.5 mm. Therefore, the minimum total width wh of the heater is $$wh = w1 + 2 \cdot w2 + 2 \cdot w3$$
$$= 0.8 + 2 \times 0.8 + 2 \times 0.5$$
$$= 3.4 \text{ mm.}$$

Regarding the shrinkage ratio (1.23 to 1.24) by baking, the minimum heater width wh is 2.8 mm.

As for the minimum width of the oxygen sensor, lead wire for a porous electrode is 0.5 mm, and the width of the electrode needs 1.5 times the lead width (i.e., 0.75 mm). Including the widths 2·a (2×0.7 mm) of the adhering margins, the minimum width w of the sensor is 2.15 mm (about 2.2 mm). Since the oxygen sensor is heated by the heater, the minimum width of the oxygen sensor should be the same (2.8 mm) as the heater in order to effectively heat the sensor and obtain sufficient responsiveness.

test 3

Figure 9:
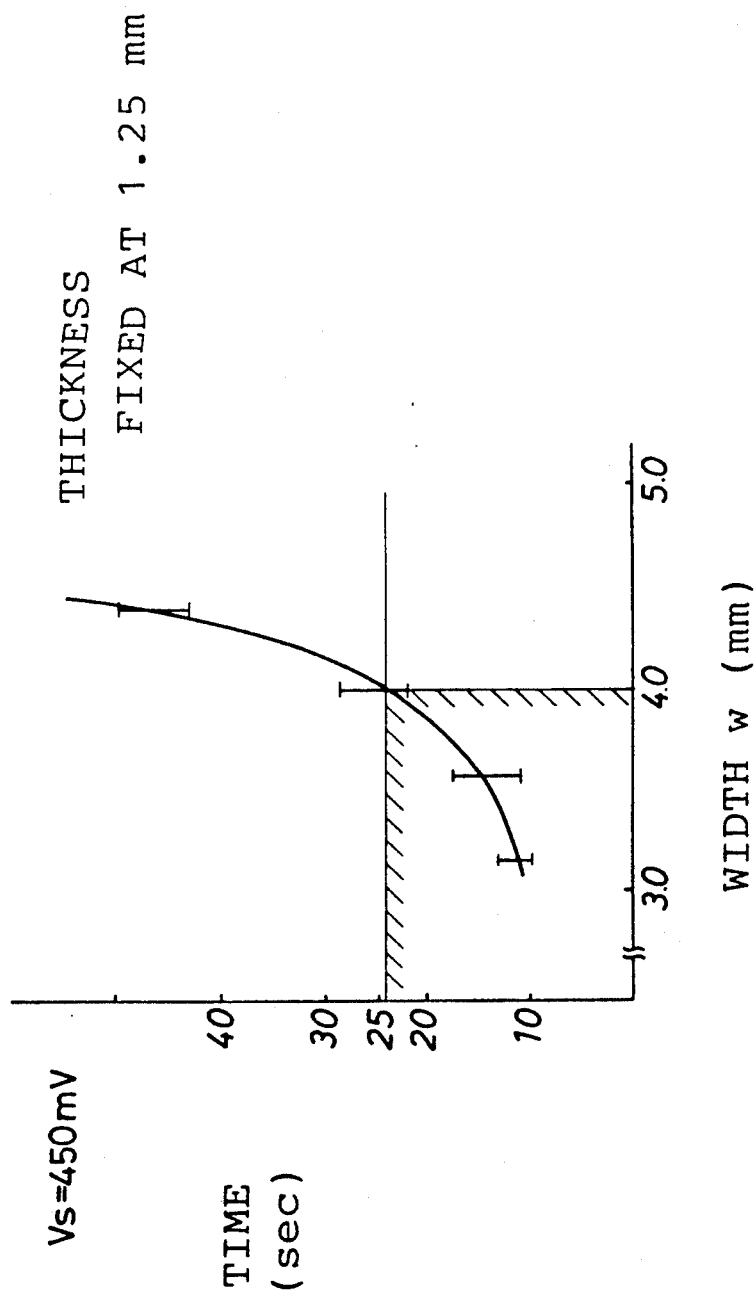
FIG. 9 is a graph showing the relationship between the width of the element and the warming-up time represented by the time required for Vs to become 450 mV.

The warming-up characteristic is tested for sensors with fixed thickness t of 1.25 mm and various widths w. The warming-up time is the time until the voltage Vs generated by the oxygen concentration cell element (cell voltage) becomes more than 450 mV. The results are shown in FIG. 9, where sensors of widths w less than 4.0 mm have good warming-up characteristic (i.e., warm up less than 25 seconds). Conventional oxygen sensors of the same type have thicknesses t of 1.45 to 1.8 mm and widths w of 5.5 to 7 mm, and take more than 90 seconds to develop the voltage of 450 mV.

test 4

Figure 10:
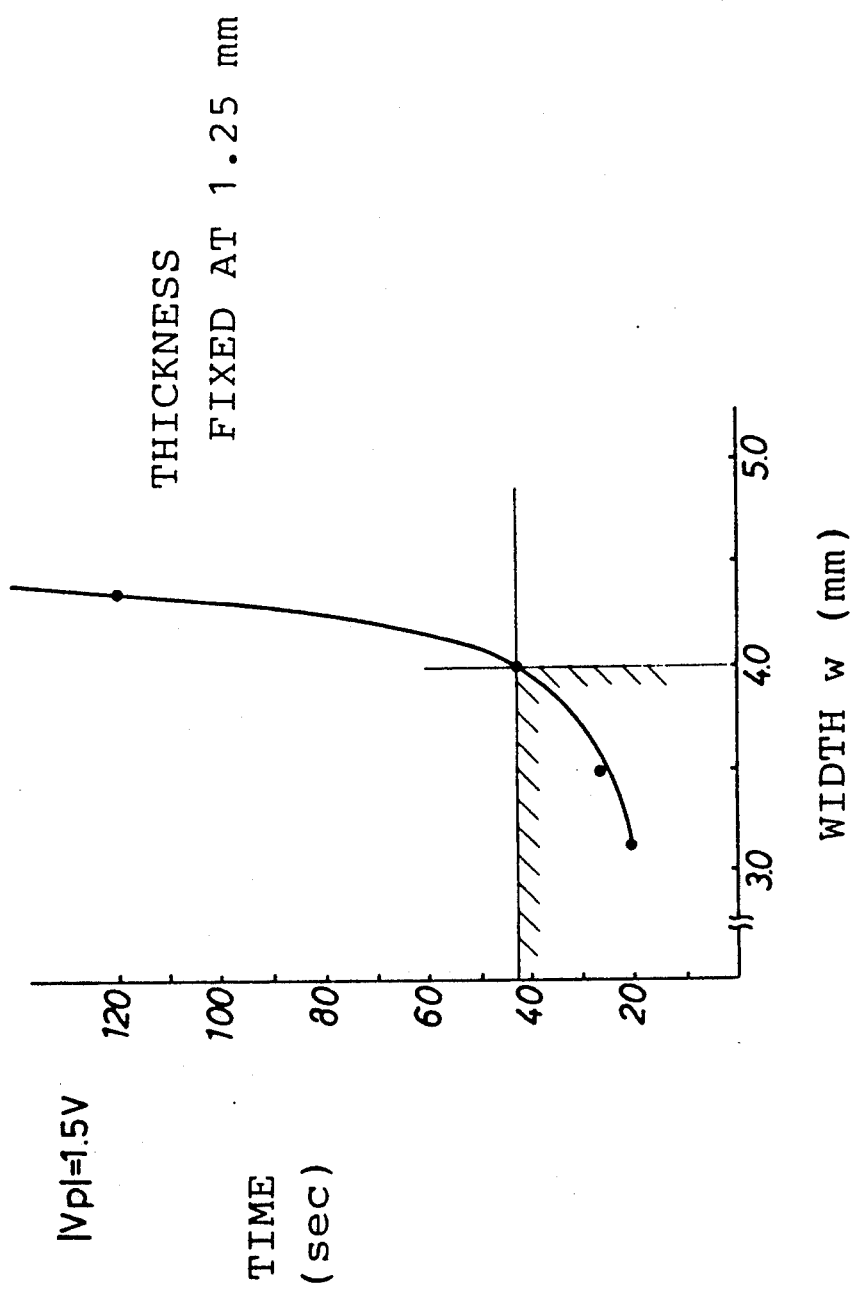
FIG. 10 is a graph showing the relationship between the width of the element and the warming-up time represented by the time required for |Vp| to become 1.5 V.

Another warming-up test is made by measuring the time until the pump voltage Vp become higher than 1.5 V. FIG. 10 shows the results where sensors of widths w less than 4.0 mm have good warming-up characteristic with less than 42 seconds. Conventional sensors described above requires more than 120 seconds to develop 1.5 V pump voltage.

test 5

Figure 11:
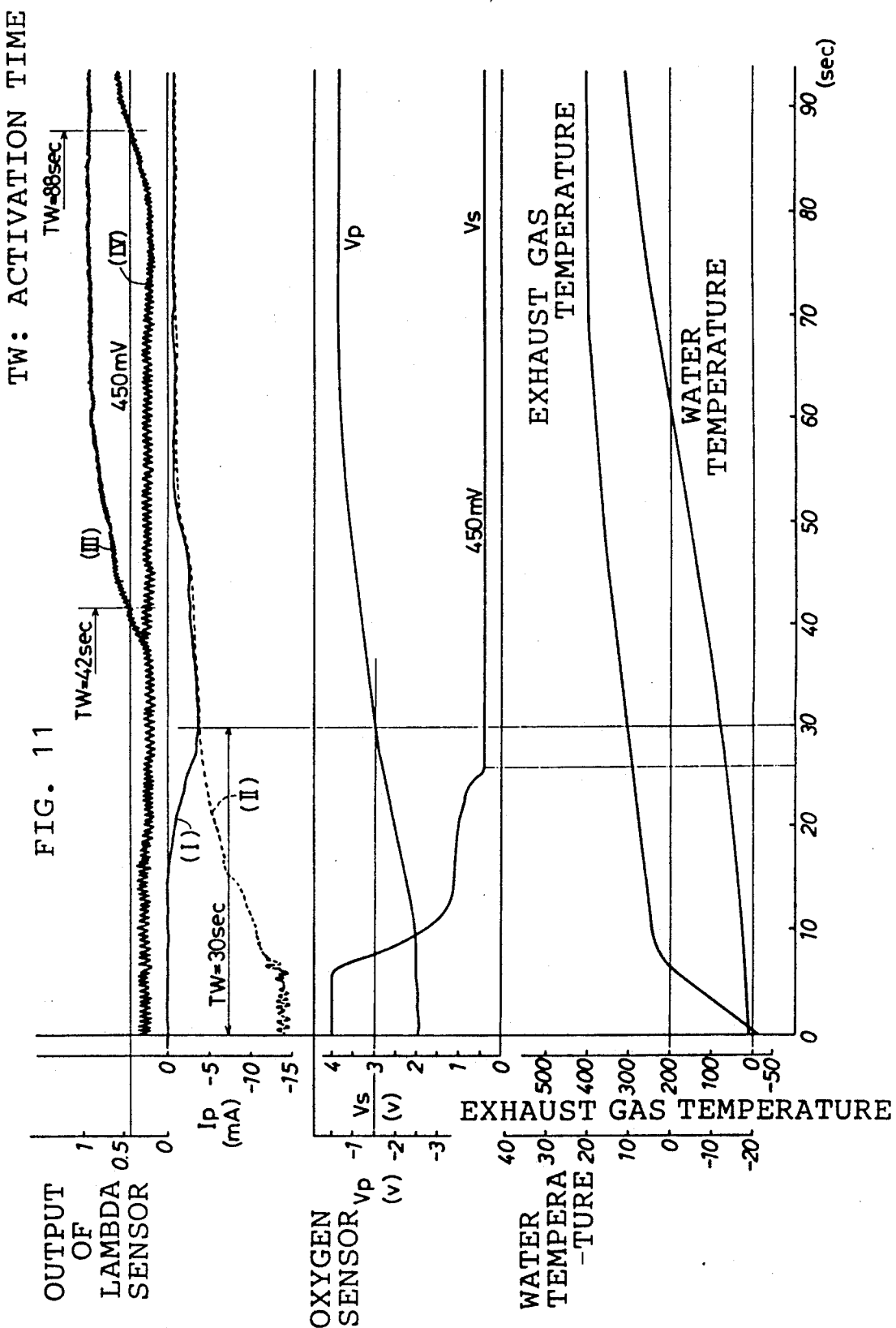
FIG. 11 shows a timing chart during the warming up of oxygen sensors.

Warming-up test of various sensors is performed on an actual 1.6 liter, 4-cycle internal combustion engine. The embodiment of the present invention is a full-range oxygen sensor (designated by I) in which the heater is applied 13 V. Comparative sensors are: a full-range oxygen sensor having an always heating heater (II); a lambda oxygen sensor having a heater (III); and a lambda oxygen sensor without heater (IV). FIG. 11 shows changes in pump voltage Vp that is applied to the oxygen pump element 16, cell voltage Vs, water temperature and exhaust gas temperature during the warming-up period of the engine. The embodiment (I) takes only 26 seconds before the cell voltage Vs reaches 450 mV, and 30 seconds before the pump voltage Vp reaches 1.5 V. An activation time is defined by the time until the output of a sensor becomes equal to that of the always-heated sensor (II). The activation time of the embodiment (I) is 30 seconds which is shorter than that of comparative lambda sensors, 42 and 48 seconds for (III) and (IV), respectively.

Following tests are for testing responsiveness and accuracy of the oxygen measurement. Optimal dimensions of the oxygen sensors are derived from the tests.

test 6

Figure 12:
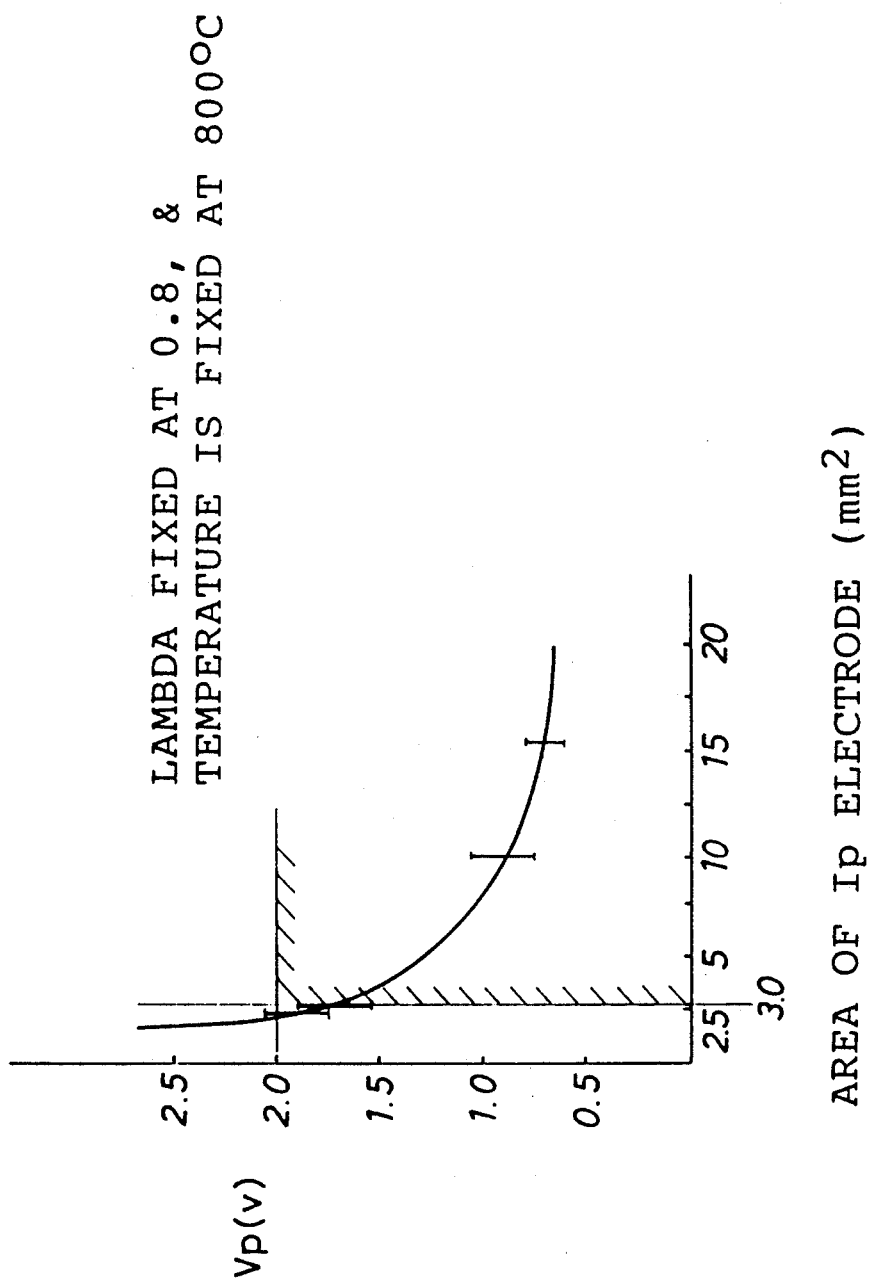
FIG. 12 is a graph showing the relationship between the area of the Ip-electrode and Vp.

This test teaches the favorable area of electrodes of the oxygen pump element. Pump voltage Vp of sensors having various electrode areas is measured with the air/fuel ratio of the object gas fixed at 0.8 (i.e., lambda=0.8), and the temperature at 800° C. FIG. 12 shows the result where electrode area greater than 3.0 mm² produces a favorable pump voltage Vp of less than 2.0 V. As mentioned before, the width of electrode needs 1.5 times the width of its lead wire. Thus, if the practical minimum lead width is 0.5 mm, the electrode width is 0.75 mm, and, consequently, the length of the electrode is 3.0/0.75=4 mm.

test 7

Figure 13:
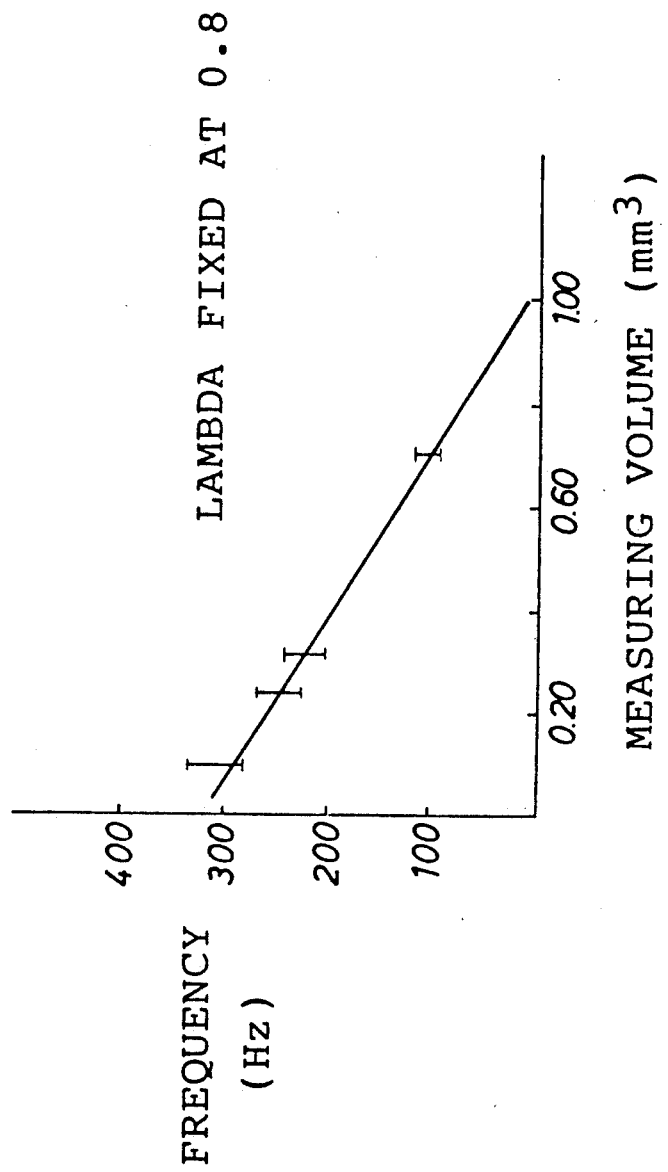
FIG. 13 is a graph showing the relationship between the measurement volume of the gas diffusion chamber and the highest operable frequency.

This test teaches favorable volume of the gas diffusion chamber that shows sufficient responsiveness to the change in the object gas (frequency characteristic). The measure of the responsiveness is the frequency of the change when a gain (ΔVp/ΔIp decibel) is %0 (i.e., ΔVp/ΔIp=1). FIG. 13 shows the result where smaller chamber volume yields better (higher) frequency characteristic. Since practical engines require the frequency greater than 10 Hz, chamber volume of 0.05 to 1.0 mm³ is preferable for responding to such rapid change.

test 8

Figure 14:
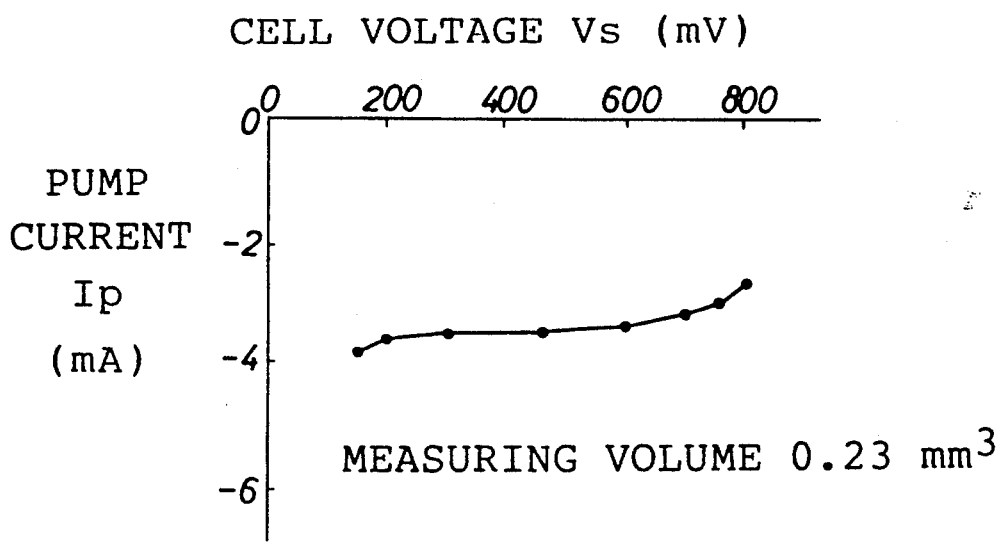
FIG. 14 is a graph showing measurement accuracy when the measurement volume is 0.23 mm$^3$.
Figure 15:
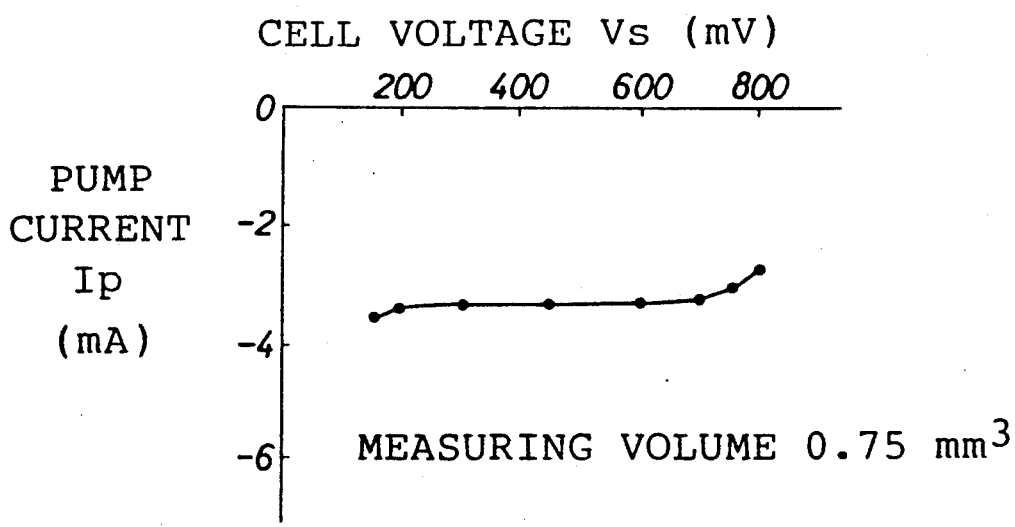
FIG. 15 is a graph showing measurement accuracy when the measurement volume is 0.75 mm$^3$.

This test teaches the measurement accuracy of oxygen sensors. Relationship between the pump current Ip and the cell voltage Vs is measured for object gases of various air/fuel ratios. Sensors of high accuracy produce Vs-Ip curves having steep change-over point (Z shaped curves) and such curves are preferred in this test. FIG. 14 is the curve for the oxygen sensor having chamber volume of 0.23 mm$^3$, and FIG. 15 is for volume of 0.75 mm$^3$, both of which are within the favorable range determined in test 7. Both sensors show steep line at the change-over point, which promises high measurement accuracy.

Since, as mentioned in test 6, the electrode area should be smaller than 3 mm$^2$, and the chamber volume is the product of the area and the thickness of the gas diffusion chamber (or the gap length), the chamber thickness should be between 20 to 100 microns. Among that, 30 to 100 microns is preferable for better measurement accuracy and quicker responsiveness. If the chamber thickness is less than 20 microns, gas diffusion speed is regulated by the small thickness so that the Vs-Ip curve will not show the steep change-over point.

test 9

Here the optimal value of the margin width a, which is, as shown in FIG. 1, the margin between an electrode and the edge of the electrolyte plate for adhering the sensor and the heater. Sensors having fixed width w of 4.0 mm, fixed thickness t of 1.25 mm, and various margin widths a are subjected to the repeated-heating test. The result shown in FIG. 16 teaches that the margin width a greater than 0.7 mm yields strong resistance to repeated thermal-shocks (i.e., does not cause separation after 200 cycles).

As seen in the tests, the oxygen sensors of the present invention have strong resistance to many cycles of rapid-heating and rapid-cooling. This shows that the sensors can be heated very rapidly after start of the engine, which enables earlier feedback control of the combustion. The reduced size of the gas diffusion chamber increases the frequency characteristic of the oxygen sensor to the change in the oxygen content of the object gas.

When the thickness t of the oxygen sensor is between 0.7 to 1.25 mm, preferably 0.9 to 1.15 mm, and the width w is between 2.8 to 4.0 mm, the sensor has a very strong resistance against repeated thermal-shocks, i.e., the lamination of the elements does not break, so that no leakage of the object gas from the gas diffusion chamber occurs after long time use. The reduced size also shortens the warming-up time so that earlier start of the feedback control of the engine is possible.

On the other hand, the dimensions are not too small to cause manufacturing problems. If the substrate electrolyte plate of the oxygen sensor is too small, the solvent in the material paste for the electrodes comes in the raw material sheet for the substrate plate so that the raw material sheet deforms. Further, moderate size assures very stable quality of the products.

What is claimed is:

1. An oxygen sensor comprising:
   an oxygen pump element having a first solid electrolyte plate and two porous electrodes, one on each surface of the first solid electrolyte plate,
   an oxygen concentration cell element having a second solid electrolyte plate and two porous electrodes, one on each surface of the second electrolyte plate, and
   a heater adjacent to at least one of the oxygen pump element and the oxygen concentration cell element,
   wherein:
   a spacer is formed between the oxygen pump element and the oxygen concentration cell element,
   a gas diffusion chamber is surrounded by the two porous electrodes facing the gas diffusion chamber and the spacer,
   a gas diffusion path is formed at the spacer and connects the gas diffusion chamber and the ambience of the oxygen sensor,
   a porous member is disposed along said path to regulate diffusion therealong,
   a shield layer is attached to the oxygen concentration cell element for shielding a one of the two porous electrodes of the oxygen concentration cell element external to the gas diffusion chamber from contact with ambient object gas,
   the thickness of the oxygen sensor is between 0.7 and 1.25 mm, and the width of the oxygen sensor is between 2.8 and 4.0 mm,
   the gas diffusion path has a resistance against gas flow,
   the volume of the gas diffusion chamber is between 0.05 and 1.0 mm$^3$,
   the thickness of the gas diffusion chamber is between 20 and 100 microns,
   the area of the electrode of the oxygen pump element facing the gas diffusion chamber is greater than 3.0 mm$^2$,
   there is provided a peripheral margin between a periphery of the shield layer and a periphery of said porous electrode of the oxygen concentration cell element external to the gas diffusion chamber, a width of the peripheral margin being greater than 0.7 mm, and
   oxygen gas in the gas diffusion chamber is transported to said one of the two porous electrodes of the oxygen concentration cell element external to the gas diffusion chamber through the electrolyte plate and the other electrode of the oxygen concentration cell element, and an internal reference source is created in one of the two porous electrodes external to the gas diffusion chamber by maintaining a voltage between the two porous electrodes of the oxygen concentration cell element at a predetermined value or maintaining a current flow through the oxygen pump element at a predetermined value.

* * * * *